United States Patent [19]

Saville

[11] Patent Number: Plant 6,952

[45] Date of Patent: Jul. 25, 1989

[54] MINIATURE ROSE PLANT NAMED SAVASHEL

[75] Inventor: F. Harmon Saville, Newburyport, Mass.

[73] Assignee: Nor'East Miniature Roses, Inc., Rowley, Mass.

[21] Appl. No.: 235,456

[22] Filed: Aug. 23, 1988

[51] Int. Cl.[4] ..... A01H 5/00

[52] U.S. Cl. ..... Plt./7

[58] Field of Search ..... Plt./7, 9

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and unusual orange pink-salmon colored miniature rose.

1 Drawing Sheet

SUMMARY OF THE INVENTION

The present invention relates to a new and distinct variety of rose plant of the miniature rose class, which was discovered by me in a controlled planting area and which is a sport (mutation) of the miniature rose known as Savswet ("Spice Drop"). The varietal denomination of this new rose is "Savashel".

Among the novel characteristics possessed by this new variety which distinguishes it from its parent from which it is a mutation and all other varieties of which I am aware are its flower size and flower coloring which appears in general tonality at a distance as orange pink-salmon. Flowers of its parent are about ½-inch and the flower size of the new variety are about 1-inch in diameter. Flowers are long lasting on the plant and after cutting. Asexual reproduction by propagation by cuttings of the new variety as performed in Essex County, Mass. shows that the foregoing and other distinguishing characteristics come true to form and are established and transmitted through succeeding propagations.

BRIEF DESCRIPTION OF DRAWING

The accompanying drawing shows typical specimens of the vegetative growth and flowers of the new variety in different stages of development and depicted in color as nearly true as it is reasonably possible to make the same in a color illustration of this character.

DESCRIPTION OF PREFERRED EMBODIMENT

The following is a detailed description of my new variety, with color terminology in accordance with The Royal Horticultural Society Color Chart (R.H.S.C.C.) The terminology used in color description herein refers to plate numbers in the aforementioned Color Chart, e.g., "48D" is plate 48D of The Royal Horticultural Society Color Chart.

Parentage: Sport of "Savswet" ("Spice Drop").
Class: Miniature.

The following observations are made of specimens grown outdoors in Essex County, Mass., during the month of June.

FLOWER

Blooming habit: Nearly continuous.

A. Bud:

(1) *Size.*—Medium.
(2) *Form.*—Ovate.
(3) *Color.*—As sepals divide, bud color is mainly near 48D imbued with slight yellow washing.
(4) *Sepals.*—Slightly foliated, longer than bud.
(5) *Peduncle.*—Length — about ⅝ inch. Aspect — straight. Strength — erect. Color — near 144B.

Bloom:

(1) *Size.*—Average size when fully expanded — about 1-inch.
(2) *Borne.*—Several together in large sprays.
(3) *Form.*—Cupped at first, becoming flat. Some outer petals reflex and quill to points; inner petals roll under; petals tend to have pointed apices.
(4) *Petalage.*—Number of petals under normal conditions — about 35 to 38.
(5) *Color.*—After sepals fall and petals unfurl, predominant flower color viewing petals' top surface is near 38B to 38A and between 38A and 37A where petals bunch. Outer petals tend toward near 36A and petal undersurface appears near 37B to 37A. Color near point of petal attachment is near 8B. General tonality from a distance appears as orange pink-salmon. As flowers age, orange pink coloring becomes soft or pale pink and light pink tones lighten still more.

C. Petals:

(1) *Texture.*—Medium.
(2) *Appearance.*—Inside velvety and outside satiny.
(3) *Form.*—Broad, fan shaped with pointed apices.
(4) *Arrangement.*—Regularly arranged, imbricated.
(5) *Petaloids in center.*—Few.
(6) *Persistence.*—Persistent.
(7) *Fragrance.*—Slight.
(8) *Lasting quality.*—Long lasting on plant and as cut flower.

REPRODUCTIVE ORGANS

A. Stamens, filaments and anthers:
*Arrangement and color.*—Regularly arranged around styles. Color — filaments near 8B.

B. Pollen:
*Color.*—Near 8B.

C. Styles: Even, medium length.

D. Stigmas:
*Color.*—Near 1B.

E. Hips: None observed.

PLANT

A. Form: Compact.

B. Growth: Vigorous, uniform branching.

*Height attained.*—About 12 to 14 inches.

C. Foliage: Compound 5 to 7 leaflets.

(1) *Size.*—Medium.

(2) *Quantity.*—Abundant.

(3) *Color.*—New foliage: Upper side — near 146A. Under side — near 148B. Old foliage: Upper side — near 147A. Under side — near to 138A.

(4) *Shape.*—Oval, pointed.

(5) *Texture.*—Upper side is glossy; under side is matte.

(6) *Edge.*—Serrate to double serrate.

(7) *Serration.*—Ordinary.

(8) *Leaf stem.*—Color — near 146C. Under side — 146D.

(9) *Stipules.*—Relatively long, smooth.

(10) *Resistance to disease.*—Blackspot — Good. Mildew — Good. Rust — Good.

D. Wood:

(1) *New wood.*—Color — near 144A. Bark — smooth.

(2) *Old wood.*—Color — near 144A. Bark — smooth.

E. Thorns:

(1) *Thorns.*—Quantity (main stalk) — ordinary. On laterals from stalk — ordinary. Form — long, thin, pointed, slanted slightly downward. Length — medium. Color — near 146D. Position — irregular.

(2) *Prickles.*—None.

F. Winter hardiness: Needs protection in severe climates.

I claim:

1. A new and distinct variety of rose plant of the miniature rose class, substantially as shown and described, characterized particularly by orange pink-salmon flowers which are larger than the parent plant of which it's a sport.

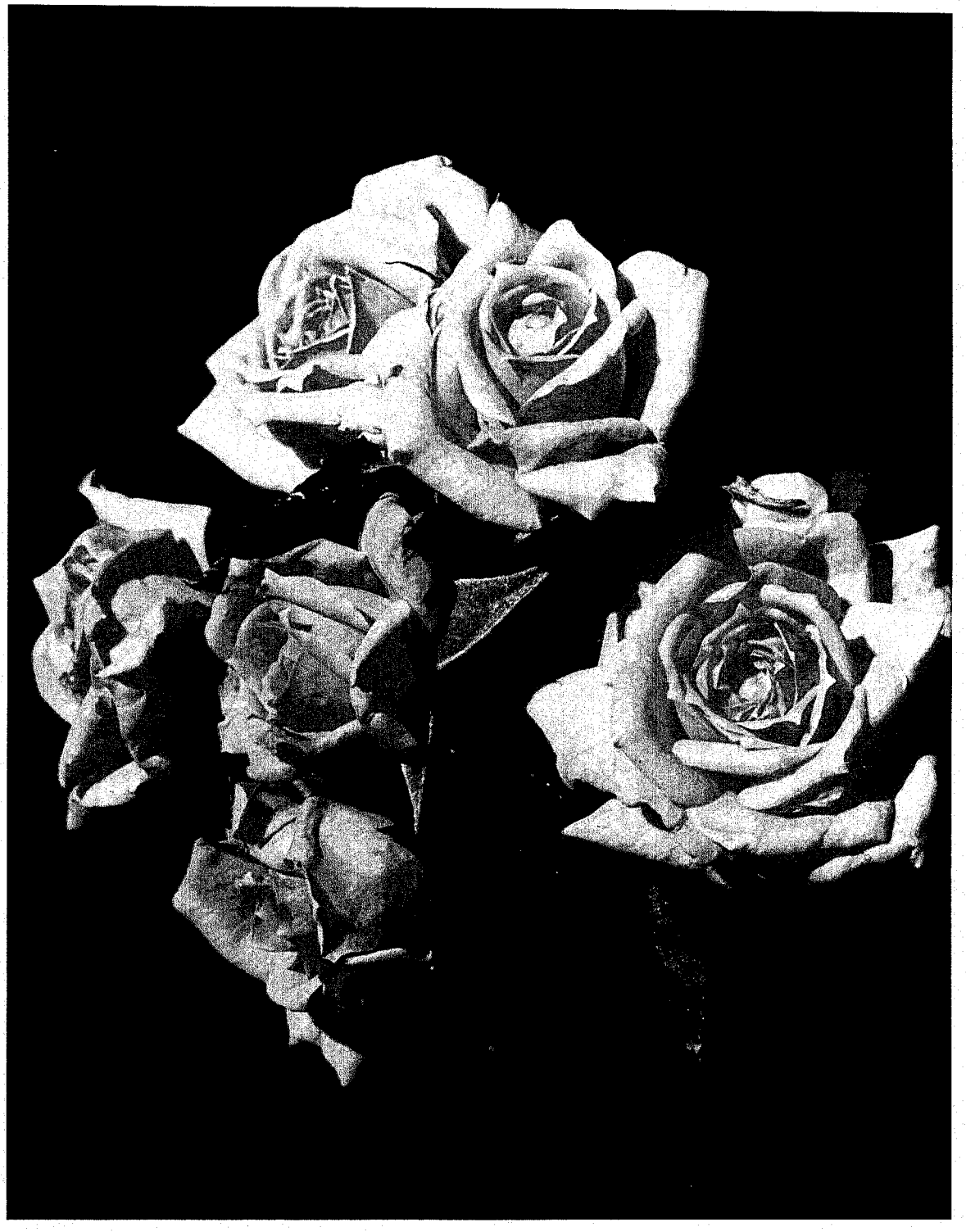

* * * * *